(12) United States Patent
Cho et al.

(10) Patent No.: US 11,883,584 B2
(45) Date of Patent: Jan. 30, 2024

(54) AEROSOL GENERATING DEVICE AND AN OPERATION METHOD THEREOF

(71) Applicant: KT&G CORPORATION, Daejeon (KR)

(72) Inventors: Byung Sung Cho, Gwangmyeong-si (KR); Won Kyeong Lee, Guri-si (KR); Jong Sub Lee, Seongnam-si (KR); Dae Nam Han, Seongnam-si (KR)

(73) Assignee: KT&G CORPORATION, Daejeon (KR)

( * ) Notice: Subject to any disclaimer, the term of this patent is extended or adjusted under 35 U.S.C. 154(b) by 854 days.

(21) Appl. No.: 16/965,634

(22) PCT Filed: Apr. 17, 2020

(86) PCT No.: PCT/KR2020/005182
§ 371 (c)(1),
(2) Date: Jul. 29, 2020

(87) PCT Pub. No.: WO2020/222450
PCT Pub. Date: Nov. 5, 2020

(65) Prior Publication Data
US 2021/0016028 A1 Jan. 21, 2021

(30) Foreign Application Priority Data

Apr. 30, 2019 (KR) .................. 10-2019-0050986

(51) Int. Cl.
*A61M 15/06* (2006.01)
*A61M 15/00* (2006.01)

(52) U.S. Cl.
CPC ........ *A61M 15/06* (2013.01); *A61M 15/0025* (2014.02); *A61M 15/0098* (2014.02);
(Continued)

(58) Field of Classification Search
CPC .......... A24F 40/53; A24F 40/50; A24F 40/10; A61M 15/06
See application file for complete search history.

(56) References Cited

U.S. PATENT DOCUMENTS 5,372,148 A 12/1994 McCafferty et al.
5,388,594 A 2/1995 Counts et al.
(Continued)

FOREIGN PATENT DOCUMENTS

CN 107752130 A 3/2018
CN 207411489 U 5/2018
(Continued)

OTHER PUBLICATIONS

Office Action dated Apr. 6, 2023 from the Chinese Patent Office in Application No. 202080001238.X.
(Continued)

*Primary Examiner* — Deanna K Hall
(74) *Attorney, Agent, or Firm* — Sughrue Mion, PLLC (57) ABSTRACT

According to some embodiments, there is disclosed an aerosol generating device which includes: a main body including a controller and a battery; and a cartridge detachably coupled to the main body, wherein the controller periodically detects whether the cartridge is coupled to the main body while the aerosol generating device operates in a first mode, determines whether a preset period of time has elapsed based on the cartridge being determined to have been separated from the main body, and switches the aerosol generating device from the first mode to a second mode based on whether the cartridge is coupled to the main body before the preset period of time elapses.

12 Claims, 6 Drawing Sheets

(52) U.S. Cl.
CPC ... *A61M 2205/33* (2013.01); *A61M 2205/502* (2013.01); *A61M 2205/8212* (2013.01)

(56) References Cited

U.S. PATENT DOCUMENTS

| | | |
|---|---|---|
| 10,701,973 B2 | 7/2020 | Lee |
| 10,820,620 B2 | 11/2020 | Saygili |
| 10,881,144 B2 | 1/2021 | Batista et al. |
| 2011/0226236 A1 | 9/2011 | Buchberger |
| 2014/0014126 A1 | 1/2014 | Peleg et al. |
| 2017/0231277 A1 | 8/2017 | Mironov et al. |
| 2020/0093185 A1 | 3/2020 | Lim |

FOREIGN PATENT DOCUMENTS

| | | |
|---|---|---|
| EP | 2 201 850 A1 | 6/2010 |
| JP | 7-184627 A | 7/1995 |
| KR | 10-1069342 B1 | 10/2011 |
| KR | 10-2018-0103878 A | 9/2018 |
| KR | 10-2018-0111845 A | 10/2018 |
| KR | 10-1908058 B1 | 10/2018 |
| KR | 10-2019-0015224 A | 2/2019 |
| WO | 2018/216961 A1 | 11/2018 |

OTHER PUBLICATIONS

International Search Report dated Dec. 11, 2020, issued by the International Searching Authority in application No. PCT/KR2020/005182.
Extended European Search Report dated Nov. 8, 2021, issued by the European Patent Office in application No. 20739837.1.

AEROSOL GENERATING DEVICE AND AN OPERATION METHOD THEREOF

CROSS-REFERENCE TO RELATED APPLICATIONS

This application is a National Stage of International Application No. PCT/KR2020/005182 filed on Apr. 17, 2020, which claims priority from Korean Patent Application No. 10-2019-0050986 filed on Apr. 30, 2019.

TECHNICAL FIELD

The present disclosure relates to an aerosol generating device and an operation method thereof.

BACKGROUND ART

Recently, the demand for alternative methods to overcome the shortcomings of general cigarettes has increased. For example, there is a growing demand for a method of generating aerosol by heating an aerosol generating material, rather than by combusting cigarettes.

Generally, an aerosol generating device includes a cartridge containing an aerosol-generating material and a main body supporting the cartridge. The aerosol generating device may heat the aerosol generating material retained in the cartridge by supplying power to the cartridge using the main body.

The aerosol generating device may have a coupling structure that the cartridge and the main body are detachable, so the cartridge can be replaced after the aerosol generating material is exhausted. However, the cartridge may be unintentionally separated from the main body while a user smokes using the aerosol-generating device. In this case, a conventional aerosol generating device does not resume a preheating operation even if the user unintentionally detaches the cartridge and immediately re-couples it to the main body. Therefore, in order for the user to smoke again, an additional operation such as turning off the aerosol generating device and then turning it on again is required. In order to increase user convenience, the heating operation needs to be resumed without additional operation when the user re-couples the cartridge to the main body after the cartridge has been unintentionally separated from the main body.

DISCLOSURE

Technical Solution

Various embodiments provide an aerosol generating device and a method of operation thereof. For example, the aerosol-generating device and the method periodically detect whether the cartridge is coupled to the main body while the aerosol generating device is operating in the first mode, determine whether a preset period of time has elapsed from the time the cartridge was separated when it is determined that the cartridge has been separated from the main body as a result of the detection, and continuously detect whether the cartridge is coupled to the main body until the preset period of time elapses. The technical solutions to be achieved by the present disclosure are not limited to the technical solutions as described above, and other technical solutions may be inferred from the following embodiments.

Advantageous Effects

The present disclosure may provide an aerosol generating device and an operation method thereof. The aerosol generating device according to the present disclosure may periodically detect whether the cartridge is coupled to the main body when the aerosol generating device is operating in the first mode (hereinafter, "on mode") and determine whether a preset period of time has elapsed from the time the cartridge was separated when it is determined that the cartridge has been separated from the main body as a result of the detection. In addition, the aerosol generating device may continuously detect whether the cartridge is re-coupled to the main body until the preset period of time elapses, and may perform or resume a preheating operation by supplying power to the cartridge without additional input when it is determined that the cartridge has been re-coupled to the main body before the preset period of time elapses. Otherwise, the aerosol generating device switches to the second mode (hereinafter, "off mode") in which minimal power is consumed without monitoring whether the cartridge is coupled to the main body.

Here, the preset period of time may be set to a time long enough for the user to re-couple the cartridge to the main body, but not too long because the user may have separated the cartridge from the main body with the intention of terminating smoking. Therefore, the preheating operation may be resumed without user's additional action other than re-coupling the cartridge to the main body when the cartridge is unintentionally separated from the main body. Accordingly, user convenience may be improved.

In addition, the aerosol generating device according to the present disclosure may output a notification through a user interface when it is determined that the cartridge has been separated from the main body. Thus, when the cartridge is unintentionally detached from the main body, the user may easily notice that the cartridge is not properly coupled to the main body.

BEST MODE

An aerosol generating device according to an aspect of the present disclosure may include a main body including a controller and a battery; and a cartridge detachably coupled to the main body, wherein the controller periodically detects whether the cartridge is coupled to the main body while the aerosol generating device operates in a first mode, determines whether a preset period of time has elapsed based on the cartridge being determined to have been separated from the main body, and switches the aerosol generating device from the first mode to a second mode based on whether the cartridge is coupled to the main body before the preset period of time elapses.

The controller may perform a preheating operation by supplying power to the cartridge based on the cartridge being coupled to the main body before the preset period of time elapses.

The controller may switch the aerosol generating device from the first mode to the second mode based on the cartridge being not coupled to the main body before the preset period of time elapses.

The controller may not perform periodic detection of whether the cartridge is coupled to the main body when the aerosol generation device is operating in the second mode.

The aerosol generating device may further include a user interface including at least one of a display for outputting visual information, a motor for outputting tactile information, and a speaker for outputting sound information, and the controller may output a notification through the user interface when it is determined that the cartridge has been separated from the main body.

As an example, the preset period of time may be set in a range of 10 seconds to 45 seconds.

The aerosol generating device may further include a puff detecting sensor for detecting user's puff, and the controller may perform a heating operation by increasing the power supplied to the cartridge as the user's puff is detected by the puff detecting sensor.

The aerosol generating device may further include a slider movably coupled to the main body; and a position change detecting sensor for detecting movement of the slider from a first position to a second position or from the second position to the first position, and the controller may switch the aerosol generating device from the second mode to the first mode based on the slider moving from the first position to the second position and switches from the first mode to the second mode based on the slider moving from the second position to the first position.

The second mode may be a mode in which minimal power is consumed to drive the position change detecting sensor.

The first position may be a position where an end of a mouthpiece coupled to the cartridge is covered by the slider, and the second position may be a position where the end of the mouthpiece is exposed to the outside.

A method of operation of the aerosol generating device according to another aspect of the present disclosure may include periodically detecting whether the cartridge is coupled to the main body while the aerosol generating device is operating in a first mode; determining whether a preset period of time has elapsed based on the cartridge being determined to have been separated from the main body; and switching from the first mode to a second mode based on whether the cartridge is coupled to the main body before the preset period of time elapses.

Another aspect of the present disclosure may provide a computer-readable recording medium in which one or more programs including instructions for executing the method according to the second aspect.

[Mode for Invention]

With respect to the terms used to describe the various embodiments, general terms which are currently and widely used are selected in consideration of functions of structural elements in the various embodiments of the present disclosure. However, meanings of the terms can be changed according to intention, a judicial precedence, the appearance of new technology, and the like. In addition, in certain cases, a term which is not commonly used can be selected. In such a case, the meaning of the term will be described in detail at the corresponding portion in the description of the present disclosure. Therefore, the terms used in the various embodiments of the present disclosure should be defined based on the meanings of the terms and the descriptions provided herein.

In addition, unless explicitly described to the contrary, the word "comprise" and variations such as "comprises" or "comprising" will be understood to imply the inclusion of stated elements but not the exclusion of any other elements. In addition, the terms "-er", "-or", and "module" described in the specification mean units for processing at least one function and/or operation and can be implemented by hardware components or software components and combinations thereof.

As used herein, expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

It will be understood that when an element is referred to as being "connected to" or "coupled to" another element, it can be directly connected or coupled to the other element or intervening elements may be present.

Hereinafter, the present disclosure will now be described more fully with reference to the accompanying drawings, in which example embodiments of the present disclosure are shown such that one of ordinary skill in the art may easily work the present disclosure. The disclosure may, however, be embodied in many different forms and should not be construed as being limited to the embodiments set forth herein.

Hereinafter, embodiments of the present disclosure will be described in detail with reference to the drawings.

Figure 1:
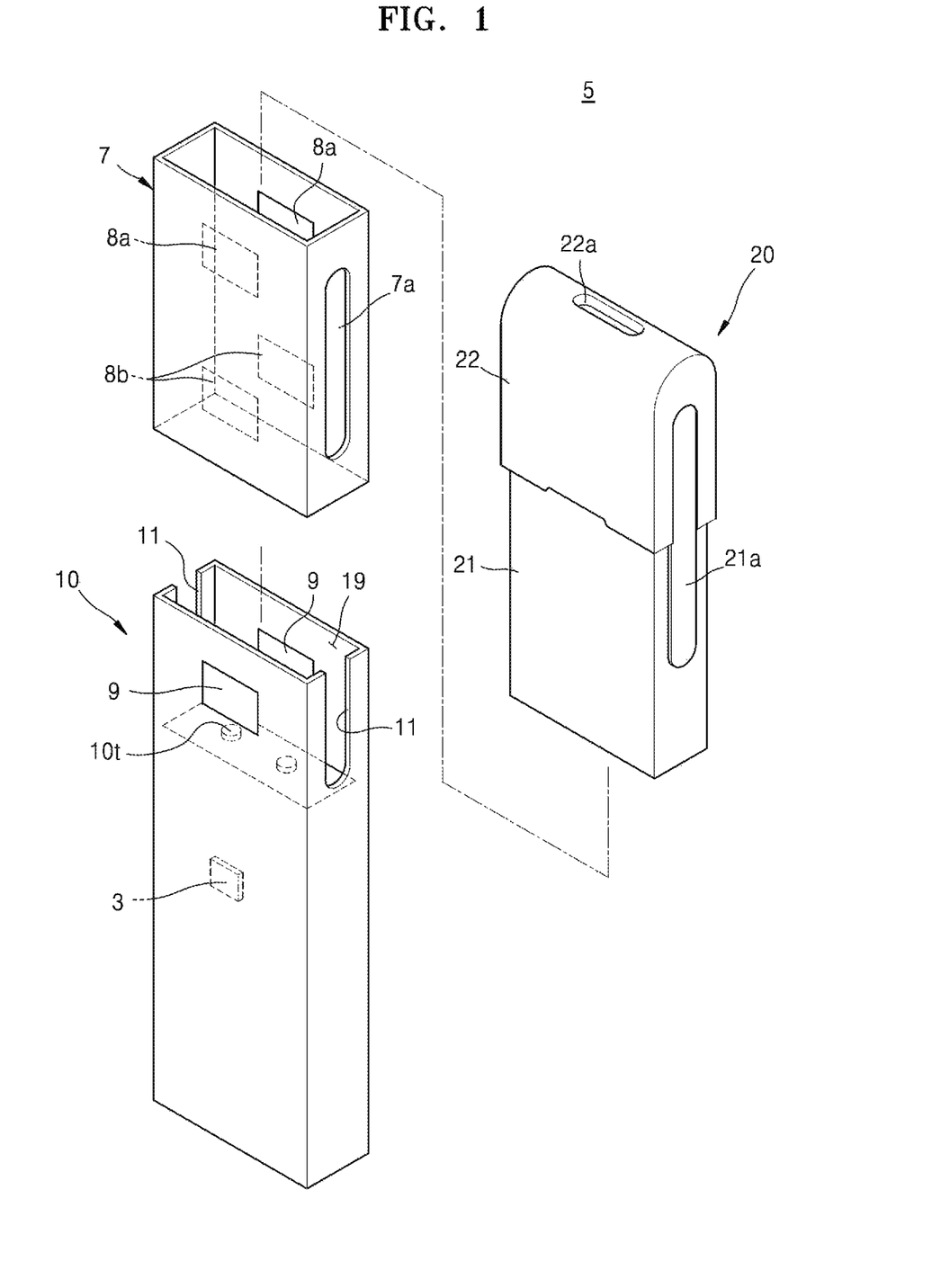
FIG. 1 is an exploded perspective view schematically illustrating a coupling relationship between a replaceable cartridge containing an aerosol generating material and an aerosol generating device including the same, according to an embodiment.

FIG. 1 is an exploded perspective view schematically illustrating a coupling relationship between a replaceable cartridge containing an aerosol generating material and an aerosol generating device including the same, according to an embodiment.

An aerosol generating device 5 according to the embodiment illustrated in FIG. 1 includes the cartridge 20 containing the aerosol generating material and a main body 10 supporting the cartridge 20.

The cartridge 20 containing the aerosol generating material may be coupled to the main body 10. A portion of the cartridge 20 may be inserted into an accommodation space 19 of the main body 10 so that the cartridge 20 may be mounted on the main body 10.

The cartridge 20 may contain an aerosol generating material in at least one of a liquid state, a solid state, a gaseous state, and a gel state. The aerosol generating material may include a liquid composition. For example, the liquid composition may be a liquid including a tobacco-containing material having a volatile tobacco flavor component, or a liquid including a non-tobacco material.

For example, the liquid composition may include one component of water, solvents, ethanol, plant extracts, spices, flavorings, and vitamin mixtures, or a mixture of these components. The spices may include menthol, peppermint, spearmint oil, and various fruit-flavored ingredients, but are not limited thereto. The flavorings may include ingredients capable of providing various flavors or tastes to a user. Vitamin mixtures may be a mixture of at least one of vitamin A, vitamin B, vitamin C, and vitamin E, but are not limited thereto. In addition, the liquid composition may include an aerosol forming agent such as glycerin and propylene glycol.

For example, the liquid composition may include any weight ratio of glycerin and propylene glycol solution to which nicotine salts are added. The liquid composition may include two or more types of nicotine salts. Nicotine salts may be formed by adding suitable acids, including organic or inorganic acids, to nicotine. Nicotine may be a naturally generated nicotine or synthetic nicotine and may have any suitable weight concentration relative to the total solution weight of the liquid composition.

Acid for the formation of the nicotine salts may be appropriately selected in consideration of the rate of nicotine absorption in the blood, the operating temperature of the aerosol generating device 5, the flavor or savor, the solubility, or the like. For example, the acid for the formation of nicotine salts may be a single acid selected from the group consisting of benzoic acid, lactic acid, salicylic acid, lauric acid, sorbic acid, levulinic acid, pyruvic acid, formic acid, acetic acid, propionic acid, butyric acid, valeric acid, caproic acid, caprylic acid, capric acid, citric acid, myristic acid, palmitic acid, stearic acid, oleic acid, linoleic acid, linolenic acid, phenylacetic acid, tartaric acid, succinic acid, fumaric acid, gluconic acid, saccharic acid, malonic acid, and malic acid, or may be a mixture of two or more acids selected from the above-described group, but is not limited thereto.

The cartridge 20 may be operated by an electrical signal or a wireless signal transmitted from the main body 10 to perform a function of generating aerosol by converting the phase of the aerosol generating material inside the cartridge 20 to a gaseous phase. The aerosol may refer to a gas in which vaporized particles generated from an aerosol generating material are mixed with air.

For example, in response to receiving the electrical signal from the main body 10, the cartridge 20 may convert the phase of the aerosol generating material by heating the aerosol generating material by, for example, an ultrasonic vibration method or an induction heating method. In an embodiment, the cartridge 20 may include its own power source and generate aerosol based on an electric control signal or a wireless signal received from the main body 10.

The cartridge 20 may include a liquid storage 21 accommodating the aerosol generating material therein, and an atomizer performing a function of converting the aerosol generating material of the liquid storage 21 to aerosol.

When the liquid storage 21 "accommodates the aerosol generating material" therein, it means that the liquid storage 21 functions as a container simply holding an aerosol generating material and that the liquid storage 21 includes therein an element impregnated with (i.e., containing) an aerosol generating material, such as a sponge, cotton, fabric, or porous ceramic structure.

The atomizer may include, for example, a liquid delivery element (e.g., wick) for absorbing the aerosol generating material and maintaining the same in an optimal state for conversion to aerosol, and a heater heating the liquid delivery element to generate aerosol.

The liquid delivery element may include at least one of, for example, a cotton fiber, a ceramic fiber, a glass fiber, and porous ceramic.

The heater may include a metallic material such as copper, nickel, tungsten, or the like to heat the aerosol generating material delivered to the liquid delivery element by generating heat using electrical resistance. The heater may be implemented by, for example, a metal wire, a metal plate, a ceramic heating element, or the like. Also, the heater may be implemented by a conductive filament using a material such as a nichrome wire, and may be wound around or arranged adjacent to the liquid delivery element.

In addition, the atomizer may be implemented by a heating element in the form of a mesh or plate, which absorbs the aerosol generating material, maintains it in an optimal state for conversion to aerosol, and generates aerosol by heating the aerosol generating material. In this case, a separate liquid delivery element may not be required.

At least a portion of the liquid storage 21 of the cartridge 20 may include a transparent portion so that the aerosol generating material accommodated in the cartridge 20 may be visually identified from the outside. The liquid storage 21 may include a protruding window 21a protruding from the liquid storage 21, so that the liquid storage 21 may be inserted into a groove 11 of the main body 10 when coupled to the main body 10. A mouthpiece 22 and/or the liquid storage 21 may be entirely formed of transparent plastic or glass. Alternatively, only the protruding window 21a may be formed of a transparent material.

The main body 10 includes a connection terminal 10t arranged inside the accommodation space 19. When the liquid storage 21 of the cartridge 20 is inserted into the accommodation space 19 of the main body 10, the main body 10 may provide power to the cartridge 20 or supply a signal related to an operation of the cartridge 20 to the cartridge 20, through the connection terminal 10t.

The mouthpiece 22 is coupled to one end of the liquid storage 21 of the cartridge 20. The mouthpiece 22 is a portion of the aerosol generating device 5, which is to be inserted into a user's mouth. The mouthpiece 22 includes a discharge hole 22a for discharging aerosol generated from the aerosol generating material inside the liquid storage 21 to the outside.

The slider 7 is coupled to the main body 10 to move with respect to the main body 10. The slider 7 covers or exposes at least a portion of the mouthpiece 22 of the cartridge 20 coupled to the main body 10 by moving with respect to the main body 10. The slider 7 includes an elongated hole 7a exposing at least a portion of the protruding window 21a of the cartridge 20 to the outside.

As shown FIG. 1, the slider 7 may have a shape of a hollow container with both ends opened, but the structure of the slider 7 is not limited thereto. For example, the slider 7 may have a bent plate structure having a clip-shaped cross-section, which is movable with respect to the main body 10 while being coupled to an edge of the main body 10. In another example, the slider 7 may have a curved semi-cylindrical shape having a curved arc-shaped cross section.

The slider 7 may include a magnetic body for maintaining the position of the slider 7 with respect to the main body 10 and the cartridge 20. The magnetic body may include a permanent magnet or a material such as iron, nickel, cobalt, or an alloy thereof.

The magnetic body may include two first magnetic bodies 8a facing each other, and two second magnetic bodies 8b facing each other. The first magnetic bodies 8a are arranged to be spaced apart from the second magnetic bodies 8b in a longitudinal direction of the main body 10 (i.e., the direction in which the main body 10 extends), which is a moving direction of the slider 7.

The main body 10 includes a fixed magnetic body 9 arranged on a path along which the first magnetic bodies 8a and the second magnetic bodies 8b of the slider 7 move as the slider 7 moves with respect to the main body 10. Two fixed magnetic bodies 9 of the main body 10 may be mounted to face each other with the accommodation space 19 therebetween.

The slider 7 may be stably maintained in positions where an end of the mouthpiece 22 is covered or exposed, by magnetic force acting between the fixed magnetic body 9 and the first magnetic body 8a or between the fixed magnetic body 9 and the second magnetic body 8b.

The main body 10 includes a position change detecting sensor 3 arranged on the path along which the first magnetic body 8a and the second magnetic body 8b of the slider 7 move as the slider 7 moves with respect to the main body 10. The position change detecting sensor 3 may include, for example, a Hall integrated circuit (IC) that uses the Hall effect to detect a change in a magnetic field, and may generate a signal based on the detected change.

In the aerosol generating device 5 according to the above-described embodiments, the main body 10, the cartridge 20, and the slider 7 have approximately rectangular cross-sectional shapes when viewed in the longitudinal direction, but in the embodiments, the shape of the aerosol generating device 5 is not limited. The aerosol generating device 5 may have, for example, a cross-sectional shape of a circle, an ellipse, a square, or various polygonal shapes. In addition, the aerosol generating device 5 is not necessarily limited to a structure that extends linearly, and may be curved in a streamlined shape or bent at a preset angle to be easily held by the user.

Figure 2:
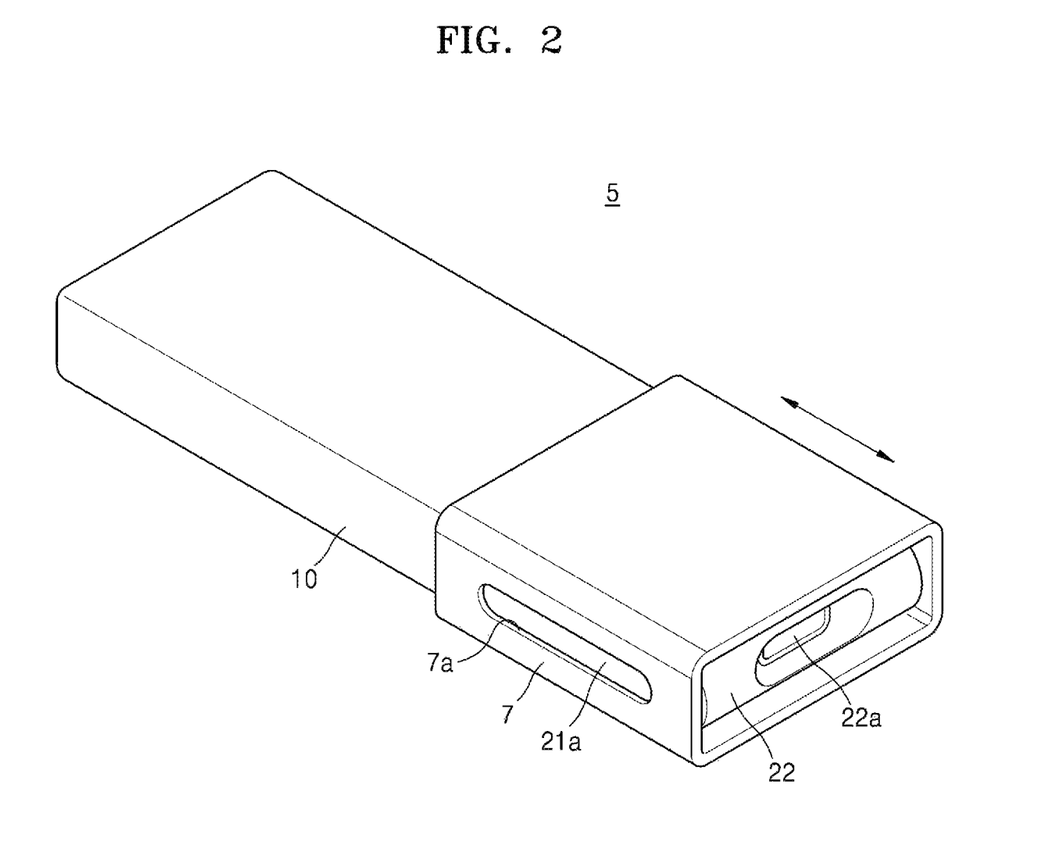
FIG. 2 is a perspective view of an example operating state of the aerosol generating device according to the embodiment illustrated in FIG. 1.

FIG. 2 is a perspective view of an example operating state of the aerosol generating device according to the embodiment illustrated in FIG. 1.

In FIG. 2, the slider 7 at a position where the end of the mouthpiece 22 of the cartridge coupled to the main body 10 is covered. In this state, the mouthpiece 22 may be safely protected from external impurities and kept clean. In addition, when the slider 7 is moved to the first position, the aerosol generating device 5 may operate in an Off mode. In the Off mode, power is not supplied to the cartridge and only minimal power is consumed to drive the position change detecting sensor.

Accordingly, the aerosol generating device 5 may detect movement of the slider 7 by driving the position change detecting sensor while consuming only minimal power when operating in the Off mode, and when the slider 7 is moved from the first position to a second position which will be described later, the Off mode may be switched to an On mode.

The user may check the remaining amount of aerosol generating material contained in the cartridge by visually checking the protruding window 21a of the cartridge through the elongated hole 7a of the slider 7. The user may move the slider 7 in the longitudinal direction of the main body 10 to use the aerosol generating device 5.

Figure 3:
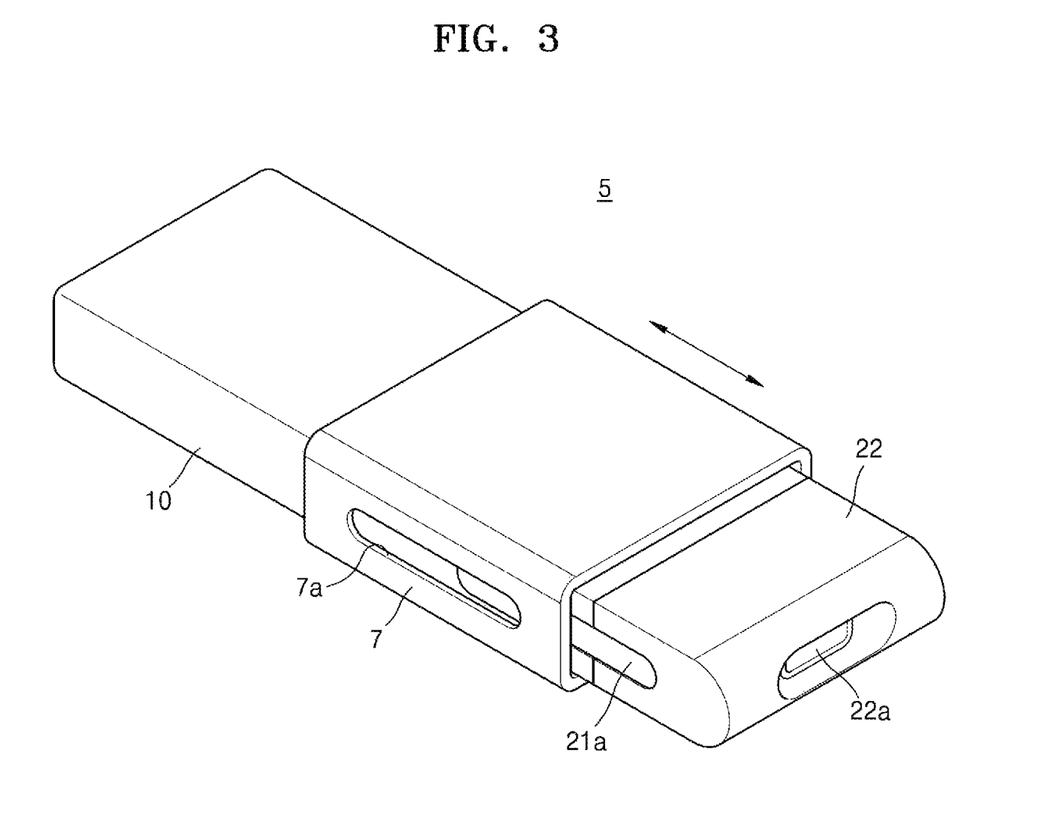
FIG. 3 is a perspective view of another example operating state of the aerosol generating device according to the embodiment illustrated in FIG. 1.

FIG. 3 is a perspective view of another example operating state of the aerosol generating device according to the embodiment illustrated in FIG. 1.

In FIG. 3, the operating state is shown in which the slider 7 is moved to a position where the end of the mouthpiece 22 of the cartridge coupled to the main body 10 is exposed to the outside. The position at which the slider 7 exposes the end of the mouthpiece 22 of the cartridge coupled to the main body 10 to the outside may be referred to as the second position. In the state in which the slider 7 is moved to the second position, the user may puff the aerosol discharged through the discharge hole 22a of the mouthpiece 22 by inserting the mouthpiece 22 into the mouth of the user.

In addition, the aerosol generating device 5 may operate in the On mode while the slider 7 is moved to the second position. The On mode is a mode for supplying power to the cartridge, and may include a preheating mode and a heating mode, which will be described later. The preheating mode may be a mode of preheating the aerosol generating material by supplying a first amount of power to the cartridge as a preparation process for vaporizing the aerosol generating material contained in the cartridge, and the heating mode may be a mode of heating the aerosol generating material by supplying a second amount of power which is greater than the first amount power to the cartridge so that the aerosol generating material contained in the cartridge is vaporized. Meanwhile, this is only an example. A profile of the amount of power supplied to the cartridge in the preheating mode and the heating mode may be set differently. Accordingly, it will be easily understood by one of ordinary skill in the art that the second amount of power may be lower than the first amount of power.

The aerosol generating device 5 may detect the movement of the slider 7 by driving the position change detecting sensor even when operating in the On mode and may switch to the Off mode when the slider 7 is moved from the second position to the first position.

Even when the slider 7 is moved to the second position, the user may visually check the remaining amount of the aerosol generating material contained in the cartridge because the protruding window 21a of the cartridge is exposed to the outside through the elongated hole 7a of the slider 7.

Figure 4:
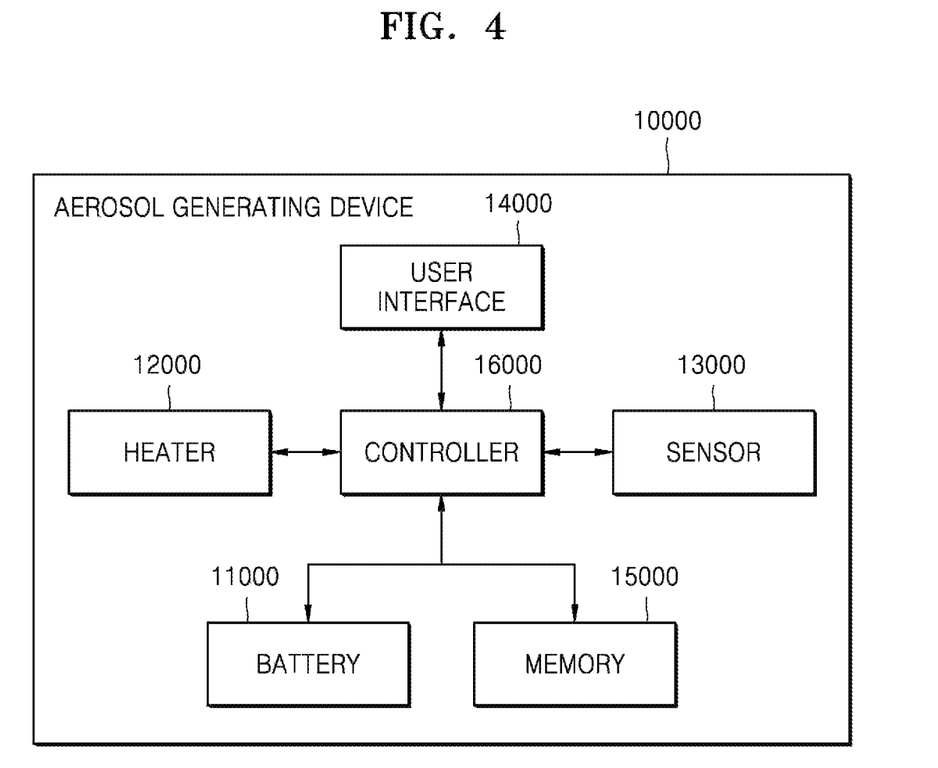
FIG. 4 is a block diagram illustrating hardware components of the aerosol generating device according to an embodiment.

FIG. 4 is a block diagram illustrating hardware components of the aerosol generating device according to an embodiment.

Referring to FIG. 4, the aerosol generating device 10000 may include a battery 11000, a heater 12000, a sensor 13000, a user interface 14000, a memory 15000, and a controller 16000. However, the internal structure of the aerosol generating device 10000 is not limited to the structures illustrated in FIG. 4. Also, it will be understood by one of ordinary skill in the art that some of the hardware components shown in FIG. 4 may be omitted or new components may be added according to the design of the aerosol generating device 10000.

In an embodiment where the aerosol generating device 10000 includes a main body without a cartridge, the components shown in FIG. 4 may be located in the main body. In another embodiment where the aerosol generating device 10000 includes a main body and a cartridge, the components shown in FIG. 4 may be located in the main body and/or the cartridge.

The battery 11000 supplies electric power to be used for the aerosol generating device 10000 to operate. For example, the battery 11000 may supply power such that the heater 12000 may be heated. In addition, the battery 11000 may supply power required for operation of other components of the aerosol generating device 10000, such as the sensor 13000, the user interface 14000, the memory 15000, and the controller 16000. The battery 11000 may be a rechargeable battery or a disposable battery. For example, the battery 11000 may be a lithium polymer (LiPoly) battery, but is not limited thereto.

The heater 12000 receives power from the battery 11000 under the control of the controller 16000. The heater 12000 may receive power from the battery 11000 and heat a cigarette inserted into the aerosol generating device 10000, or heat the cartridge mounted on the aerosol generating device 10000.

The heater 12000 may be located in the main body of the aerosol generating device 10000. Alternatively, the heater 12000 may be located in the cartridge. When the heater 12000 is located in the cartridge, the heater 12000 may receive power from the battery 11000 located in the main body and/or the cartridge.

The heater 12000 may be formed of any suitable electrically resistive material. For example, the suitable electrically resistive material may be a metal or a metal alloy including titanium, zirconium, tantalum, platinum, nickel, cobalt, chromium, hafnium, niobium, molybdenum, tungsten, tin, gallium, manganese, iron, copper, stainless steel, or nichrome, but is not limited thereto. In addition, the heater 12000 may be implemented by a metal wire, a metal plate on which an electrically conductive track is arranged, or a ceramic heating element, but is not limited thereto.

In an embodiment, the heater 12000 may be included in the cartridge. The cartridge may include the heater 12000, the liquid delivery element, and the liquid storage. The aerosol generating material accommodated in the liquid storage may be absorbed by the liquid delivery element, and the heater 12000 may heat the aerosol generating material absorbed by the liquid delivery element, thereby generating aerosol. For example, the heater 12000 may include a material such as nickel or chromium, and may be wound around or arranged adjacent to the liquid delivery element.

In another embodiment, the heater 12000 may heat the cigarette inserted into the accommodation space of the aerosol generating device 10000. As the cigarette is accommodated in the accommodation space of the aerosol generating device 10000, the heater 12000 may be located inside and/or outside the cigarette. Accordingly, the heater 12000 may generate aerosol by heating the aerosol generating material in the cigarette.

Meanwhile, the heater 12000 may include an induction heater. The heater 13000 may include an electrically conductive coil for heating a cigarette or the cartridge by an induction heating method, and the cigarette or the cartridge may include a susceptor which may be heated by the induction heater.

The aerosol generating device 10000 may include at least one sensor 13000. A result sensed by the sensor 13000 is transmitted to the controller 16000, and the controller 16000 may control the aerosol generating device 10000 by controlling the operation of the heater, restricting smoking, determining whether a cigarette (or a cartridge) is inserted, displaying a notification, etc.

For example, the sensor 13000 may include a puff detecting sensor. The puff detecting sensor may detect a user's puff based on a temperature change, a flow change, a voltage change, and/or a pressure change.

In addition, the at least one sensor 13000 may include a temperature sensor. The temperature sensor may detect a temperature of the heater 12000 (or an aerosol generating material). The aerosol generating device 10000 may include a separate temperature sensor for sensing a temperature of the heater 12000, or the heater 12000 itself may serve as a temperature sensor without a separate temperature sensor. Alternatively, a separate temperature sensor may be further included in the aerosol generating device 10000 while the heater 12000 serves as a temperature sensor.

The sensor 13000 may include a position change detecting sensor. The position change detecting sensor may detect a change in a position of the slider which is coupled to the main body and slides along the main body.

The user interface 14000 may provide the user with information about the state of the aerosol generating device 10000. For example, the user interface 14000 may include various interfacing devices, such as a display or a light emitter for outputting visual information, a motor for outputting haptic information, a speaker for outputting sound information, input/output (I/O) interfacing devices (for example, a button or a touch screen) for receiving information input from the user or outputting information to the user, terminals for performing data communication or receiving charging power, and/or communication interfacing modules for performing wireless communication (for example, Wi-Fi, Wi-Fi direct, Bluetooth, near-field communication (NFC), etc.) with external devices.

The memory 15000 may store various data processed or to be processed by the controller 16000. The memory 15000 may include various types of memories, such as dynamic random access memory (DRAM), static random access memory (SRAM), read-only memory (ROM), electrically erasable programmable read-only memory (EEPROM), etc.

The memory 15000 may store an operation time of the aerosol generating device 10000, the maximum number of puffs, the current number of puffs, at least one temperature profile, data on a user's smoking pattern, etc.

The controller 16000 may control overall operations of the aerosol generating device 10000. The controller 16000 may include at least one processor. A processor can be implemented as an array of a plurality of logic gates or can be implemented as a combination of a general-purpose microprocessor and a memory in which a program executable in the microprocessor is stored. It will be understood by one of ordinary skill in the art that the processor can be implemented in other forms of hardware.

The controller 16000 analyzes a result of the sensing by the sensor 13000, and controls processes that are to be performed subsequently.

The controller 16000 may control power supplied to the heater 12000 so that the operation of the heater 12000 is started or terminated, based on the result of the sensing by the sensor 13000. In addition, based on the result of the sensing by the sensor 13000, the controller 16000 may control the amount of power supplied to the heater 12000 and the time at which the power is supplied, so that the heater 12000 is heated to a predetermined temperature or maintained at an appropriate temperature.

In an embodiment, the controller 16000 may set a mode of the heater 12000 to a pre-heating mode to start the operation of the heater 12000 after receiving a user input to the aerosol generating device 10000. In addition, the controller 16000 may switch the mode of the heater 12000 from the pre-heating mode to the heating mode after detecting a user's puff by using the puff detecting sensor. The heating mode may be a mode in which the amount of power supplied to the heater 12000 is increased than the preheating mode so that the aerosol generating material is vaporized. Meanwhile, the controller 16000 may convert the mode of the heater 12000 to the heating mode by detecting user's puff without additional user's input. Accordingly, user convenience may be increased. In addition, the controller 16000 may stop supplying power to the heater 12000 when the number of puffs reaches a preset number after counting the number of puffs by using the puff detecting sensor.

The controller 16000 may control the user interface 14000 based on the result of the sensing by the at least one sensor 13000. For example, when the number of puffs counted by the puff detecting sensor reaches a preset number, the controller 16000 may notify the user by using the user interface 14000 (e.g., a light emitter, a motor, a speaker, etc.) that the aerosol generating device 10000 will soon be terminated.

Although not illustrated in FIG. 4, the aerosol generating device 10000 may be combined with a separate cradle to form an aerosol generating system. For example, the cradle may be used to charge the battery 11000 of the aerosol generating device 10000. For example, the aerosol generating device 10000 may be supplied with power from a battery of the cradle to charge the battery 11000 of the aerosol generating device 10000 while being accommodated in an accommodation space of the cradle.

The controller 16000 may periodically detect whether the cartridge is coupled to the main body while the aerosol generating device 10000 operates in the On mode. If the aerosol generating device 10000 continues to operate in the On mode while the cartridge is not coupled to the main body, unnecessary power may be consumed. Accordingly, the controller 16000 periodically detects whether the cartridge is coupled to the main body. If it is determined that the cartridge is coupled to the main body as a result of the detection, the controller 16000 may perform the preheating operation by supplying power to the heater 12000 included in the cartridge. If it is determined that the cartridge has been separated from the main body, the controller may switch the operation mode of the aerosol generating device 10000.

However, a situation in which the cartridge is unintentionally separated from the main body may occur while the user is smoking using the aerosol-generating device 10000. In this case, if the operation mode of the aerosol generating device 10000 is immediately switched to the Off mode, the user must perform an additional action to move the slider 7 to the first position and then back to the second position in order to smoke again. This is because the preheating operation is not resumed even if the user immediately re-couples the unintentionally separated cartridge to the main body. This may be cumbersome for the user. Thus, in a situation where it is determined that the cartridge is unintentionally separated from the main body, it is desirable that the preheating operation is resumed without additional operation when the user re-couples the cartridge to the main body.

To this regard, the controller 16000 may determine whether a preset period of time has elapsed from the time the cartridge was separated, when it is determined that the cartridge has been separated from the main body as a result of the detection. And the controller 16000 may continuously detect whether the cartridge is coupled to the main body until the preset period of time elapses. The controller 16000 may perform or resume the preheating operation by supplying power to the cartridge even if there is no additional input when it is determined that the cartridge has been re-coupled to the main body before the preset period of time elapses. Accordingly, user convenience may be improved.

The preset period of time may be set to a time that is long enough for the user to re-couple the cartridge to the main body, but not too long because the user may have separated the cartridge from the main body with the intention of terminating smoking. For example, when the preset period of time is less than 10 seconds, the preset period may be insufficient time for the user to recognize that the cartridge has been separated from the main body and then to re-couple the cartridge to the main body. In addition, when the preset period of time is more than 45 seconds, the aerosol-generating device 10000 may consume unnecessary power to continuously detect whether the cartridge is coupled to the main body, considering that the user may have separated the cartridge from the main body with the intention of terminating of smoking.

Therefore, for example, the preset period of time may be set within a range of 10 seconds to 45 seconds. However, it is not necessarily limited thereto. In another example, the preset period of time may be set within a range of 15 seconds to 40 seconds, 25 seconds to 35 seconds, etc.

Meanwhile, the controller 16000 may switch the operation mode of the aerosol generating device 10000 from the On mode to the Off mode when it is determined that the preset period of time has elapsed. When the aerosol generating device 10000 operates in the Off mode, the controller 16000 may prevent unnecessary power consumption by no longer performing periodic detection of whether the cartridge is coupled to the main body.

The controller 16000 may output a notification through the user interface 14000 when it is determined that the cartridge has been separated from the main body. For example, the controller 16000 may output visual information indicating that the cartridge has been separated from the main body using a display or a light emitter and/or may output haptic information indicating that the cartridge has been separated from the main body using a motor. In addition, the controller 16000 may output sound information indicating that the cartridge has been separated from the main body using a speaker. Accordingly, regardless of the user's intention, when the cartridge was separated from the main body, the user may easily notice that the cartridge is improperly coupled to the main body, and may sufficiently re-couple the cartridge with the main body within the preset period of time. In addition, when the cartridge and the main body are partially and improperly coupled, for example, due to debris between the cartridge and the main body, it may be difficult for the user to recognize this because the coupling portion of the cartridge and the main body may be covered blocked by the slider. Therefore, the notification indicating that the cartridge has been separated from the main body may be required.

Figure 5:
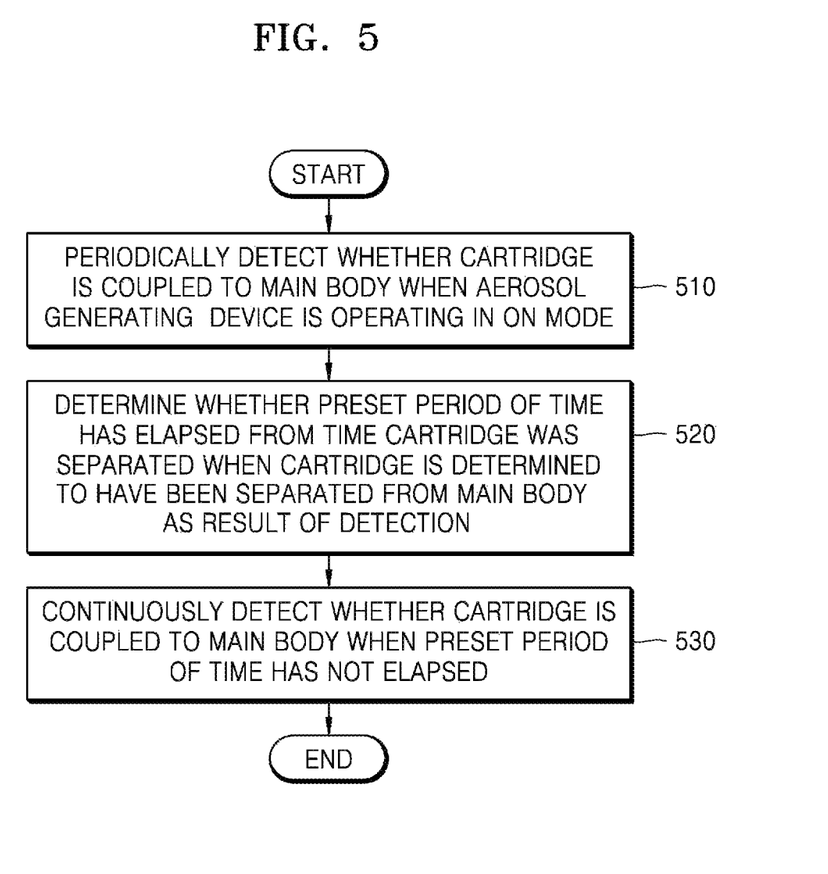
FIG. 5 is a flowchart illustrating an operation method of the aerosol generating device according to an embodiment.

FIG. 5 is a flowchart illustrating an operation method of the aerosol generating device according to an embodiment.

Referring to FIG. 5, the operation method of the aerosol generating device may include steps that are processed by the aerosol generating device 5 or the aerosol generating device 10000 illustrated in FIGS. 1 to 4. Accordingly, the above descriptions of the aerosol generating device 5 or the aerosol generating device 10000 illustrated in FIGS. 1 to 4 may also be applied to the operation method of the aerosol generating device illustrated in FIG. 5, even if omitted below.

In step 510, the aerosol generating device may periodically detect whether the cartridge is coupled to the main body when the aerosol generating device is operating in the On mode. The aerosol generating device may perform the preheating operation by supplying power to the cartridge when it is determined that the cartridge is coupled to the main body. In addition, the aerosol generating device may perform the heating operation by increasing the power supplied to the cartridge when the user's puff is detected while the cartridge is coupled to the main body.

In step 520, when it is determined that the cartridge has been separated from the main body as a result of the detection, the aerosol generating device may determine whether the preset period of time has elapsed from the time when the cartridge is separated. The preset period of time may be set long enough for the user to re-couple the cartridge to the main body, but not too long because the user may have separated the cartridge from the main body with the intention of terminating smoking. For example, the preset period may be set in the range of 10 seconds and 45 seconds. However, it is not necessarily limited thereto.

Meanwhile, the aerosol generating device may output the notification through the user interface when it is determined that the cartridge has been separated from the main body. Accordingly, when the cartridge has been unintentionally separated from the main body, the user can easily know that the cartridge is improperly coupled to the main body. Also, a sufficient amount of time may be available to re-couple the cartridge to the main body.

In step 530 the aerosol generating device may continuously detect whether the cartridge is coupled to the main body until the preset period of time elapses. The aerosol generating device may perform or resume the preheating operation by supplying power to the cartridge when it is determined that the cartridge has been re-coupled to the main body before the preset period of time expires. In this way, the preheating operation may be resumed without the user's additional operation, thereby improving user convenience.

Meanwhile, the aerosol generating device may switch the operation mode of the aerosol generating device from the On mode to the Off mode when it is determined that the preset period of time has elapsed. When the aerosol generating device operates in the Off mode, periodic detection of whether the cartridge is coupled to the main body may not be performed. In this case, the user may have intentionally separated the cartridge from the main body without the intention of smoking again within the preset period of time. Therefore, the aerosol generating device is switched to the Off mode, and unnecessary power consumption may be prevented.

Figure 6:
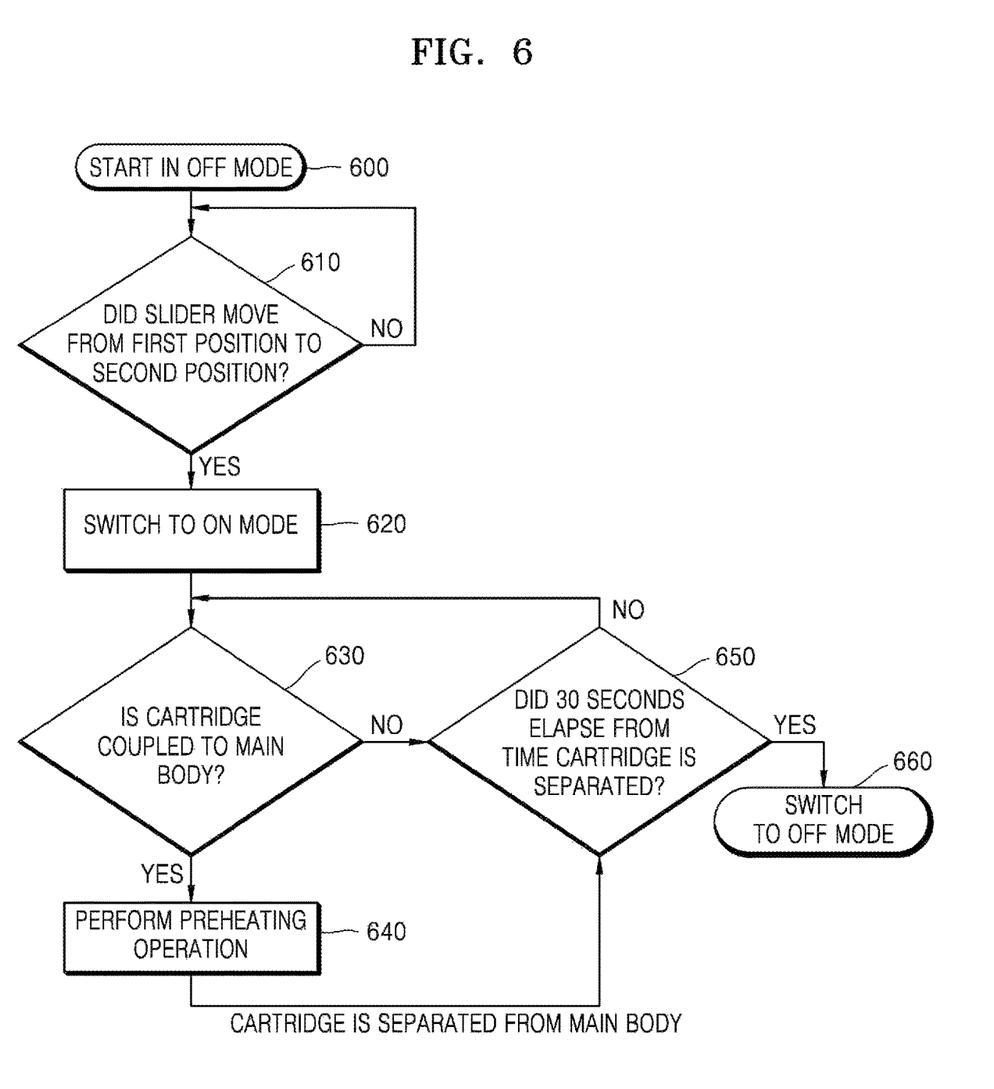
FIG. 6 is a schematic diagram illustrating an overall operation process of the aerosol generating device according to an embodiment.

FIG. 6 is a schematic diagram showing an overall operation process of the aerosol generating device according to an embodiment.

In step 600, the aerosol generating device may initially operate in the Off mode. For example, when the slider included in the aerosol generating device is in the first position where the end of the mouthpiece coupled to the cartridge is covered by the slider, the aerosol generating device may operate in the Off mode.

In step 610, the aerosol generating device may detect whether the slider has been moved from the first position to the second position where the end of the mouthpiece is exposed to the outside. Step 610 is maintained while the slider is at the first position, and the method proceeds to step 620 when the slider is moved to the second position.

In step 620, the aerosol generating device may switch to the On mode. The On mode is a mode for supplying power to the cartridge, and may include the preheating mode and the heating mode. In addition, in the On mode, it may be periodically detected whether the cartridge is coupled to the main body.

In step 630, the aerosol generating device may detect whether the cartridge is coupled to the main body. Step 640 may be performed when it is determined that the cartridge is coupled to the main body as a result of the detection, and step 650 may be performed when it is determined that the cartridge has been separated from the main body as a result of the detection.

In step 640, the aerosol generating device may perform the preheating operation by supplying power to the cartridge. Meanwhile, the cartridge may be separated from the body without the user's intention while the preheating operation is being performed by the aerosol-generating device. In this case, the method proceeds to step 650.

In step 650, the aerosol generating device may determine whether, for example, 30 seconds have elapsed after the cartridge is separated. If 30 seconds has not yet elapsed, the method proceeds to step 630, and the aerosol generating device may monitor whether the cartridge is coupled to the main body. Here, the 30 seconds is just an example, and the time period may be set differently. If 30 seconds have not yet elapsed, the method proceeds to step 660.

In step 660, the aerosol generating device may switch the operation mode from the On mode to the Off mode. In the Off mode, unlike the On mode, there is no periodic detection of whether the cartridge is coupled to the main body, and only minimal power may be consumed to detect movement of the slider from the first position to the second position or from the second position to the first position.

Meanwhile, the operation method of the aerosol generating device shown in FIGS. 5 and 6 may be recorded in a computer-readable recording medium in which one or more programs including instructions for executing the method are recorded. Examples of computer-readable recording media include magnetic media such as hard disks, floppy disks, and magnetic tapes, optical media such as CD-ROMs and DVDs, magneto-optical media such as floptical disks, ROM, RAM, and flash memory. The examples of computer-readable recording media include hardware devices specially configured to store and execute program instructions. Examples of the program instructions include high-level language code that can be executed by a computer using an interpreter, etc., as well as machine code made by a compiler.

At least one of the components, elements, modules or units (collectively "components" in this paragraph) represented by a block in the drawings such as the controller 16000 and the user interface 14000 in FIG. 4, may be embodied as various numbers of hardware, software and/or firmware structures that execute respective functions described above, according to an example embodiment. For example, at least one of these components may use a direct circuit structure, such as a memory, a processor, a logic circuit, a look-up table, etc. that may execute the respective functions through controls of one or more microprocessors or other control apparatuses. Also, at least one of these components may be specifically embodied by a module, a program, or a part of code, which contains one or more executable instructions for performing specified logic functions, and executed by one or more microprocessors or other control apparatuses. Further, at least one of these components may include or may be implemented by a processor such as a central processing unit (CPU) that performs the respective functions, a microprocessor, or the like. Two or more of these components may be combined into one single component which performs all operations or functions of the combined two or more components. Also, at least part of functions of at least one of these components may be performed by another of these components. Further, although a bus is not illustrated in the above block diagrams, communication between the components may be performed through the bus. Functional aspects of the above example embodiments may be implemented in algorithms that execute on one or more processors. Furthermore, the components represented by a block or processing steps may employ any number of related art techniques for electronics configuration, signal processing and/or control, data processing and the like.

The descriptions of the above-described embodiments are merely examples, and it will be understood by one of ordinary skill in the art that various changes and equivalents thereof may be made. Therefore, the scope of the disclosure should be defined by the appended claims, and all differences within the scope equivalent to those described in the claims will be construed as being included in the scope of protection defined by the claims.

What is claimed is:

1. An aerosol generating device comprising:
a main body including a controller and a battery; and
a cartridge detachably coupled to the main body,
wherein the controller periodically detects whether the cartridge is coupled to the main body while the aerosol generating device operates in a first mode, determines whether a preset period of time has elapsed based on the cartridge being determined to have been separated from the main body, and switches the aerosol generating device from the first mode to a second mode based on whether the cartridge is coupled to the main body before the preset period of time elapses.

2. The aerosol generating device of claim 1, wherein the controller performs a preheating operation by supplying power to the cartridge based on the cartridge being coupled to the main body before the preset period of time elapses.

3. The aerosol generating device of claim 1, wherein the controller switches the aerosol generating device from the first mode to the second mode based on the cartridge being not coupled to the main body before the preset period of time elapses.

4. The aerosol generating device of claim 3, wherein the controller does not perform periodic detection of whether the cartridge is coupled to the main body when the aerosol generation device is operating in the second mode.

5. The aerosol generating device of claim 1, further comprising a user interface including at least one of a display for outputting visual information, a motor for outputting haptic information, and a speaker for outputting sound information,
wherein the controller outputs a notification through the user interface when the cartridge has been separated from the main body.

6. The aerosol generating device of claim 1, wherein the preset period of time is set in a range of 10 seconds to 45 seconds.

7. The aerosol generating device of claim 2, further comprising a puff detecting sensor for detecting a user's puff,
wherein the controller performs a heating operation by increasing the power supplied to the cartridge based on the user's puff being detected by the puff detecting sensor.

8. The aerosol generating device of claim 1, further comprising:
a slider movably coupled to the main body such that the slider moves between a first position and a second position; and
a position change detecting sensor for detecting movement of the slider, and
the controller switches from the second mode to the first mode based on the slider moving from the first position to the second position and switches from the first mode to the second mode based on the slider moving from the second position to the first position.

9. The aerosol generating device of claim 8, wherein minimal power is consumed to drive the position change detecting sensor when aerosol generating device operates in the second mode.

10. The aerosol generating device of claim 8, wherein
an end of a mouthpiece coupled to the cartridge is covered by the slider when the slider is at the first position, and
the end of the mouthpiece is exposed to outside when the slider is at the second position.

11. A operation method of an aerosol generating device including a main body and a cartridge detachably coupled to the main body, the method comprising:
periodically detecting whether the cartridge is coupled to the main body while the aerosol generating device is operating in a first mode;
determining whether a preset period of time has elapsed based on the cartridge being determined to have been separated from the main body; and
switching from the first mode to a second mode based on whether the cartridge is coupled to the main body before the preset period of time elapses.

12. A computer-readable recording medium in which one or more programs including instructions for executing the method of claim 11 are recorded.

* * * * *